United States Patent [19]

Polansky et al.

[11] 4,249,532
[45] Feb. 10, 1981

[54] DECORATED DISPOSABLE DIAPER

[75] Inventors: Herbert Polansky, c/o George Specter 3615 Woolworth Bldg., NY, N.Y. 10007; George Spector, New York, N.Y.

[73] Assignee: Herbert Polansky, Ocean Side, N.Y.

[21] Appl. No.: 13,321

[22] Filed: Feb. 21, 1979

Related U.S. Application Data

[63] Continuation of Ser. No. 802,733, Jun. 2, 1977, abandoned.

[51] Int. Cl.³ .............................................. A61F 13/16
[52] U.S. Cl. .................................................... 128/287
[58] Field of Search .............. 128/284, 287, 270, 290; 101/35, 37, 375, 376

[56] References Cited

U.S. PATENT DOCUMENTS

| | | | |
|---|---|---|---|
| 2,580,576 | 1/1952 | Myers | 101/211 |
| 2,587,606 | 3/1952 | Dungler | 101/375 X |
| 3,013,487 | 12/1961 | Faeber | 101/181 |
| 3,295,188 | 1/1967 | Saveressing | 101/376 X |
| 3,364,049 | 1/1968 | Deck et al. | 40/615 |
| 3,842,837 | 10/1974 | Sward | 128/287 |
| 4,022,211 | 5/1977 | Timmons et al. | 128/287 |
| 4,050,463 | 9/1977 | Schaar | 128/284 |

Primary Examiner—Kyle L. Howell
Assistant Examiner—C. W. Shedd

[57] ABSTRACT

A disposable diaper that shows a decorative printed design on its one side, the design being printed in reverse and on the inner side of a transparent polyethylene sheet that forms the one side of the diaper.

1 Claim, 7 Drawing Figures

U.S. Patent
Feb. 10, 1981
4,249,532
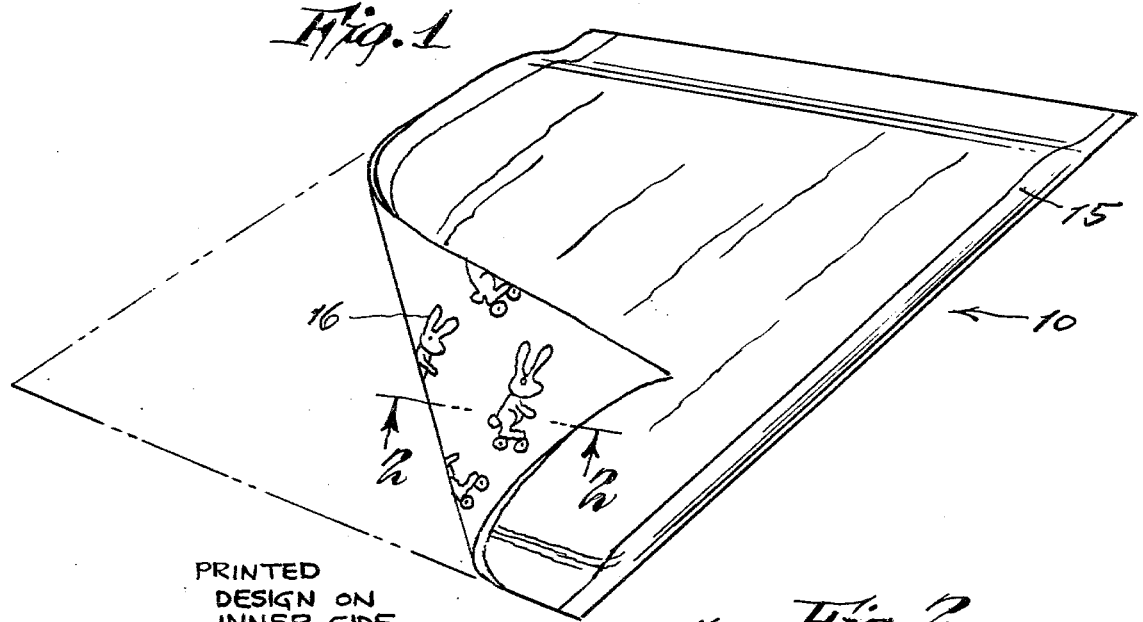
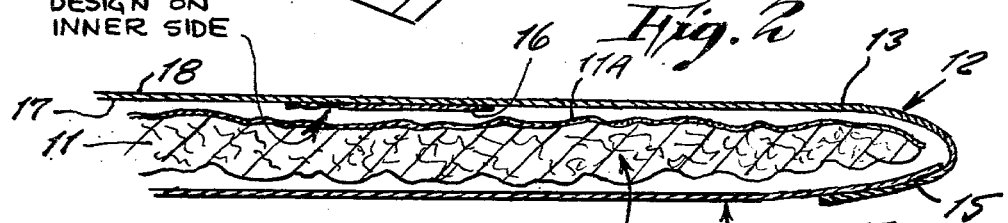
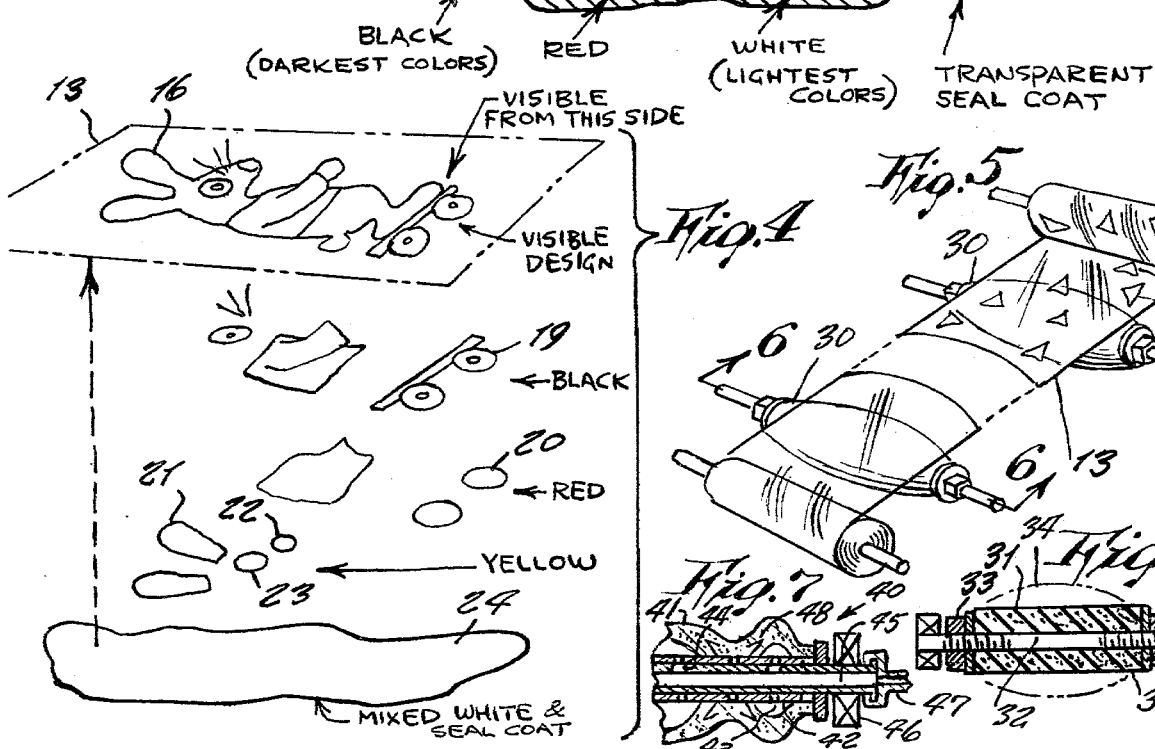
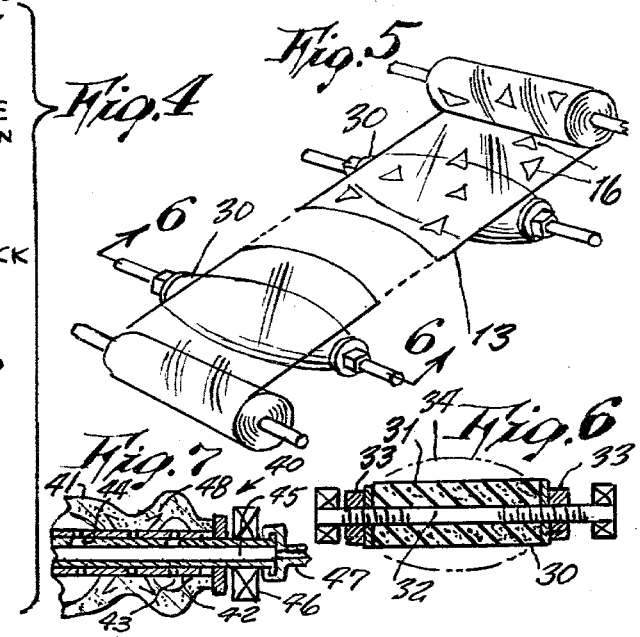

DECORATED DISPOSABLE DIAPER

This invention relates generally to infants' diapers, and is continuation of Ser. No. 802,733, filed June 2, 1977, now abandoned.

A principal object of the present invention is to provide a diaper having a decorative design printed thereon so to be more attractive in appearance and handling.

Another object is to provide a printed diaper wherein the printed design is located on an inner surface of the diaper transparent polyethylene side wall, so that the printing will not be effected by any oils or lotions applied on a babys skin, and thus not dissolve and smear on bedding or clothing.

Another object is to provide a decorative printed diaper wherein the printed design faces a wadding of the diaper and is interproofed from urine by a seal coat being applied thereupon so to not be effected thereby.

Another object is to provide disposable diaper wherein the printed polyethylene sheet used in the diaper construction is moved through the printing machine in a selectively taut condition so that a desired printing design effect can be accomplished.

Other objects are to provide a disposable diaper which is simple in design, inexpensive to manufacture, rugged in construction, easy to use and efficient in operation.

These and other objects will be readily evident upon a study of the following specification and the accompanying drawings wherein:

FIG. 1 is a perspective view of the diaper including the invention.

FIG. 2 is an enlarged cross section on line 2—2 of FIG. 1.

FIG. 3 is a further enlarged cross section of a detail of FIG. 2.

FIG. 4 is an exploded view of the color application.

FIG. 5 shows a design in which a curved roller stretches the polyethylene sheet taut during a printing process.

FIG. 6 is a cross section on line 6—6 FIG. 5 showing the roller curve being adjustable.

FIG. 7 is a fragmentary cross sectional view of a further modified design of roller used in the printing press.

Referring now to the drawing in a greater detail, and more particularly to FIGS. 1 to 3 thereof at this time, the reference numeral 10 represents a decorated disposable diaper compressed of a wadding 11 enclosed inside an envelope or case 12 consisting of a transparent polyethelene sheet 13 and an absorbent paper sheet 14, each of which is on one side of the wadding, and which is attached together with a suitable adhesive at 15. The wadding surface 11A may be preferably water and oil proofed.

In the present invention, an attractive design 16 is imprinted in various colors on and inner side 17 of the polythelene sheet 13 so to be visible from the outer side 18. It is imprinted with opaque colors, the darkest colors being applied first, and progressively toward a lightest color so that a first may be black, intermediate colors may be red, green and the like and a last colors may be yellow or white. As shown in FIG. 2, of the successively applied colors can overlap colors already applied. Thus in FIG. 4, the outlines in black first applied showing the skates 19 and the like. A red color next applied, shows the skate wheels 20 colored, all red. A next lighter color may be yellow or pink so to color the bunny ears 21, nose 22 and eyes 23 in full. Thereafter a white may be applied if so needed, and finally a seal coat 24 covers the entire printed colors so to enclose them from contact with any substance that might make the colors to run. The seal coat can include a varnish or other compound that seals. Alternatively, a seal coat can be also included with the final white coat of color, as preferred.

In use, it is now evident that the colors are protected by the seal coat from contact with substances that might make them to run. The print being on an inner side of the sheet 13, accordingly necessitates the same to be in reverse printing to the image as viewed from the outer side.

In FIGS. 5 and 6, a roller 30 is shown for use in a printing press when printing the design 16 so to maintain the sheet 13 selectively taut in order that the design have a selective sharpness. The roller 30 comprises a resilient rubber sleeve 31 on a threaded shaft 32 fitted with nuts 33 so to selectively squeeze the sleeve into a bulged condition as shown at 34 in order that the bulge applies greater pressure at the sheet 13 at certain areas, while other areas of the sheet get less pressure.

In FIG. 7 the design of FIGS. 5 and 6 is further modified by allowing change of the bulges on the roller as wished. The roller 40 includes resilient rubber sleeve 41 on a tube 42 with perforations 43 throughout its length which can be selectively aligned with perforations 44 of a hollow shaft 45 rotatable in bearings 46 and which has compressed air admitted through a rotatable coupling from a hose 47 to inflate selected portions of the sleeve 41. Lips 48 on an inner surface of the sleeve surround portions thereof exposed to perforations 43 so to form additional sealing rings against air leak from surrounded area.

While various changes may be made in the detail construction, it is understood that such changes will be within the spirit and scope of the present invention, as is defined by the appended claims.

What is claimed:

1. A decorated disposable diaper and a means for decoration thereof, said diaper comprising in combination a wadding inside an envelope comprised of a transparent polyethylene sheet having inner and outer surfaces on one side adhered to an absorbent paper sheet on an opposite side thereof, and a multi-colored design reverse printed on said inner surface of said polyethylene sheet, said printed design having a seal coat underlying said design on said inner surface, said wadding having a water and oil proofed surface adjacent said inner surface; and wherein said design comprises a first design coat of black color and a second design coat of lighter color said design further including an overlying sealing coat.

* * * * *